US012758553B2

(12) United States Patent
Heymach et al.

(10) Patent No.: US 12,758,553 B2
(45) Date of Patent: Oct. 13, 2026

(54) USE OF POZIOTINIB FOR THE TREATMENT OF CANCERS WITH NRG1 FUSIONS

(71) Applicant: Board of Regents, The University of Texas System, Austin, TX (US)

(72) Inventors: John Heymach, Houston, TX (US); Jacqulyne Robichaux, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 585 days.

(21) Appl. No.: 17/759,713

(22) PCT Filed: Jan. 29, 2021

(86) PCT No.: PCT/US2021/015686

§ 371 (c)(1),
(2) Date: Jul. 28, 2022

(87) PCT Pub. No.: WO2021/155130

PCT Pub. Date: Aug. 5, 2021

(65) Prior Publication Data

US 2023/0069749 A1 Mar. 2, 2023

Related U.S. Application Data

(60) Provisional application No. 62/967,265, filed on Jan. 29, 2020.

(51) Int. Cl.

| | |
|---|---|
| ***A61K 31/517*** | (2006.01) |
| ***A61K 39/00*** | (2006.01) |
| ***A61K 39/395*** | (2006.01) |
| ***A61P 35/00*** | (2006.01) |
| ***C07K 16/32*** | (2006.01) |
| ***C12Q 1/6886*** | (2018.01) |

(52) U.S. Cl.

CPC ...... *A61K 31/517* (2013.01); *A61K 39/39558* (2013.01); *A61P 35/00* (2018.01); *C07K 16/32* (2013.01); *C12Q 1/6886* (2013.01); *A61K 2039/505* (2013.01); *A61K 2300/00* (2013.01); *C07K 2317/92* (2013.01); *C12Q 2600/106* (2013.01)

(58) Field of Classification Search

None

See application file for complete search history.

(56) References Cited

U.S. PATENT DOCUMENTS

| | | | |
|---|---|---|---|
| 11,186,875 | B2 | 11/2021 | Carpten et al. |
| 2016/0312288 | A1 | 10/2016 | Fernandez-Cuesta et al. |
| 2018/0171412 | A1 | 6/2018 | Carpten et al. |
| 2023/0112470 | A1 | 4/2023 | Heymach et al. |
| 2023/0121116 | A1 | 4/2023 | Heymach et al. |

FOREIGN PATENT DOCUMENTS

| | | | |
|---|---|---|---|
| CN | 109476748 | A | 3/2019 |
| CN | 110291104 | A | 9/2019 |
| JP | 2014511383 | A | 5/2014 |
| JP | 2015506955 | A | 3/2015 |
| WO | WO 2008/150118 | A2 | 12/2008 |
| WO | WO 2009/042618 | A1 | 4/2009 |
| WO | WO 2012/116317 | A2 | 8/2012 |
| WO | WO 2013/113796 | A1 | 8/2013 |
| WO | WO 2015/144759 | A1 | 10/2015 |
| WO | WO 2016/201454 | A1 | 12/2016 |
| WO | WO 2017/013160 | A1 | 1/2017 |
| WO | WO 2018/094225 | A1 | 5/2018 |
| WO | WO 2018/182422 | A1 | 10/2018 |
| WO | WO 2019/051155 | A1 | 3/2019 |
| WO | WO 2019/165003 | A1 | 8/2019 |
| WO | WO 2020/005934 | A1 | 1/2020 |

OTHER PUBLICATIONS

Wang et. al. ((2018), Pan-HER-targeted approach for cancer therapy Mechanisms, recent advances and clinical prospect, Cancer Letters, 439, 113-130 (Year: 2018).*

Guo et. al. ((2019), Recent Progress in Rare Oncogenic Drivers and Targeted Therapy for Non-Small Cell Lung Cancer, OncoTargets and Therapy, 12, 10343-10360 (Year: 2019).*

Chen, Y. et al., "Research progress on drug resistance of ALK-TKIs clause," *Chinese Journal of Oncology Prev and Trat*, 9.4 (2017): 329-333.

Office Action issued in Chinese Patent Application No. 202180026290.5, dated Mar. 25, 2025.

Jones, M. R. et al., "Successful targeting of the NRG1 pathway indicates novel treatment strategy for metastatic cancer," *Annals of Oncology*, 28 (2017): 3092-3097.

Drilon, A et al., "Response to ERBB3-Directed Targeted Therapy in NRG1-Rearranged Cancers," *Cancer Discovery*, (2018): 686-695.

English translation of Office Action issued in Chinese Patent Application No. 202180026224.8, issued Jan. 2, 2024.

Extended European Search report issued in European Patent Application No. 21747692.8, dated Sep. 12, 2023.

Extended European Search report issued in European Patent Application No. 21748449.2, dated Sep. 14, 2023.

Extended European Search report issued in European Patent Application No. 21748276.9, dated Sep. 18, 2023.

Fernandez-Cuesta, L. et al., "CD74-NRGI fusions in lung adenocarcinoma," *Cancer Discovery*, 4 (2014): 415-422.

Gladstone, E. et al., "Generation and Characterization of Novel Preclinical Disease Models of NSCLC with NRG1 Rearrangements to Improve Therapy," *Journal of Thoracic Oncology*, 14.10S (2019): S334.

(Continued)

*Primary Examiner* — Juliet C Switzer
*Assistant Examiner* — Dawanna Shar-Day White
(74) *Attorney, Agent, or Firm* — pH IP Law

(57) ABSTRACT

Provided herein are methods of selecting cancer patients for treatment with poziotinib as well as methods of treating cancer patients so selected. Cancer patients are selected for treatment if their cancer has an NRG1 fusion. Selected patients are then treated with poziotinib alone or in combination with HER2/HER3 targeting antibodies.

7 Claims, 2 Drawing Sheets

(56) References Cited

OTHER PUBLICATIONS

Holbro, T. et al., "The ErbB2/ErbB3 heterodimer functions as an oncogenic unit: ErbB2 requires ErbB3 to drive breast tumor cell proliferation," *Proc. Natl. Acad. Sci. USA*, 100.15 (2003): 8933-8938.
Jones, M. R. et al., "NRGI Gene Fusions are Recurrent, Clinically Actionable Gene Rearrangements are KRAS Wild-Type Pancreatic Ductal Adenocarcinoma," *Clinical Cancer Research*, 25.15 (2019): 4674-4681.
Jonna, S. et al., "Detection of NRG1 Gene Fusions in Solid Tumors," *Clinical Cancer Research*, 25.16 (2019): 4966-4972.
Jung, Y. et al., "VAMP2-NRGI Fusion Gene is a Novel Oncogenic Driver of Non-Small-Cell Lung Adenocarcinoma," *J. Thorac. Oncol.*, 10.7 (2015): 1107-1111.
PCT International Search Report and Written Opinion issued in International Patent Application No. PCT/US2021/015686, mailed Apr. 23, 2021.
PCT Preliminary Report on Patentability issued in International Patent Application No. PCT/US2021/015686, mailed Aug. 11, 2022.
PCT International Search Report and Written Opinion issued in International Patent Application No. PCT/US2021/015662, mailed Apr. 23, 2021.
PCT Preliminary Report on Patentability issued in International Patent Application No. PCT/US2021/015662, mailed Aug. 11, 2022.
PCT International Search Report and Written Opinion issued in International Patent Application No. PCT/US2021/015704, mailed Apr. 14, 2021.
PCT Preliminary Report on Patentability issued in International Patent Application No. PCT/US2021/015704, mailed Aug. 11, 2022.
Robichaux, J. P. et al., "Mechanisms and Clinical Activity of an EGFR and HER2 Exon 20-selective Kinase Inhibitor in Non-small Cell Lung Cancer," *Nat Med.*, 24.5 (2018): 638-646.
Robichaux, J. P. et al., "Pan-Cancer Landscape and Analysis of ERBB2 Mutations Identifies Poziotinib as a Clinically Active Inhibitor and Enhancer of T-DM1 Activity," *Cell Press*, 36 (2019): 444-457.
Schram, A. M. et al., "A phase II basket study of MCLA-128, a bispecific antibody targeting the HER3 pathway, in NRG1 fusion-positivie advanced solid tumours," *Annals on Oncology*, 30.5 (2019): v317.
Shin, D. H. et al., "Dual Targeting of ERBB2/ERBB3 for the Treatment of SLC3A2-NRG1-Mediated Lung Cancer," *Molecular Cancer Therapeutics*, 17.9 (2018): 2024-2033.
Shin, D. H. et al., "Oncogenic function and clinical implications of SLC3A2-NRG1 fusion in invasive mucinous adenocarcinoma of the lung," *Oncotarget*, 7.43 (2016): 69450-69465.
Udagawa, H. et al., "HER4 and EGFR Activate Cell Signaling in NRG1 Fusion-Driven Cancers: Implications for HER2-HER3-specific Versus Pan-HER Targeting Strategies," *J Thorac Oncol.*, 19.1 (2024): 106-118.
Han, J-Y. et al., "A Phase II Study of Poziotinib in Patients with Epidermal Growth Factor Receptor (EGFR)-Mutant Lung Adenocarcinoma Who Have Acquired Resistance to EGFR-Tyrosine Kinase Inhibitors," *Cancer Res Treat.*, 49.1 (2017): 10-19.
Office Action issued in Japanese Patent Application No. 2022-545994, dated Dec. 24, 2024.
Kim, H. S. et al., "EGFR and HER3 signaling blockade in invasive mucinous lung adenocarcinoma harboring an NRGI fusion," *Lung Cancer*, 124 (2018): 71-75.
Duruisseaux, M. et al., "Targeting NRG1-Fusions in Lung Adenocarcinoma: Afatinib as a Novel Potential Treatment Strategy," Journal of Thoracic Oncology, 14.10 (2019): S563, 1 page.
Murumägi, A. et al., "Clinical implementation of precision systems oncology in the treatment of ovarian cancer based on ex-vivo drug testing and molecular profiling," Cancer Res., 79.13_Supplement (2019): 2945, 4 pages.
Keller, S. et al., "Effects of trastuzumab and afatinib on kinase activity in gastric cancer cell lines," Molecular Oncology, 12 (2018): 441-462.

* cited by examiner

USE OF POZIOTINIB FOR THE TREATMENT OF CANCERS WITH NRG1 FUSIONS

REFERENCE TO RELATED APPLICATIONS

The present application is a national phase application under 35 U.S.C. § 371 of International Application No. PCT/US2021/015686, filed Jan. 29, 2021, which claims the priority benefit of U.S. provisional application No. 62/967,265, filed Jan. 29, 2020, the entire contents of each of which are incorporated herein by reference.

BACKGROUND

1. Field

The present invention relates generally to the fields of medicine and oncology. More particularly, it concerns methods for selecting cancer patients for treatment with poziotinib, alone or in combination with HER2/HER3 targeting antibodies, as well as methods of treating cancer patients so selected.

2. Description of Related Art

NRG1 fusions occur in 0.3% of non-small cell lung cancer (NSCLC), and have been observed in several other cancer types including gallbladder (0.5%), breast (0.2%), ovarian (0.4%), and colorectal (0.1%) cancers (Jonna et al., 2019). Common NRG1 fusions partners are CD74 (29% of NRG1 fusions), ATP1B1 (10% of NRG1 fusions), and SDC4 (7% of NRG1 fusions) (Jonna et al., 2019). NRG1 binds the HER3 receptor to cause preferential hetero-dimerization with HER2 (Shin et al., 2018; Jung et al., 2015; Fernandez-Cuesta et al., 2014), one of the most potent forms of ERBB family signaling (Holbro et al., 2003). Previous reports have shown that targeting the HER2/HER3 signaling pathway can be effective in inhibiting NRG1 fusion-driven ErbB signaling (Shin et al., 2018; Fernandez-Cuesta et al., 2014; Drilon et al., 2018). Previous reports have also shown that poziotinib can inhibit both EGFR (Robichaux et al., 2018) and HER2 (Robichaux et al., 2019) mutations. However, there are no approved targeted therapies for patients with NRG1 fusions.

SUMMARY

In one embodiment, provided herein are methods of treating a patient having a cancer, the methods comprising (a) determining or having determined whether the patient's cancer has an NRG1 fusion; (b) selecting or having selected the patient for treatment with poziotinib when the patient's cancer has an NRG1 fusion; and (c) administering or having administered to the selected patient a therapeutically effective amount of poziotinib. In some aspects, step (a) comprises (i) obtaining or having obtained a biological sample from the patient; and (ii) performing or having performed an assay on the biological sample to determine the patient's cancer has an NRG1 fusion.

In one embodiment, provided herein are methods of treating a patient having a cancer, the methods comprising administering to the patient a therapeutically effective amount of poziotinib, wherein the cancer has an NRG1 fusion. In one embodiment, provided herein are compositions comprising a therapeutically effective amount of poziotinib, for use in the treatment of cancer in a patient, wherein the patient's cancer has an NRG1 fusion.

In one embodiment, provided herein are methods of selecting a patient having a cancer for treatment with poziotinib, the method comprising (a) determining or having determined whether the patient's cancer has an NRG1 fusion; (b) selecting or having selected the patient for treatment with poziotinib when the patient's cancer has an NRG1 fusion. In some aspects, step (a) comprises (i) obtaining or having obtained a biological sample from the patient; and (ii) performing or having performed an assay on the biological sample to determine the patient's cancer has an NRG1 fusion. In some aspects, the methods further comprise (c) administering or having administered to the selected patient a therapeutically effective amount of poziotinib.

In one embodiment, provided herein are methods of treating a patient having a cancer, the method comprising (a) determining or having determined whether the patient's cancer has an NRG1 fusion; (b) selecting or having selected the patient for treatment with poziotinib and a HER2/HER3 targeting antibody when the patient's cancer has an NRG1 fusion; and (c) administering or having administered to the selected patient a combined therapeutically effective amount of poziotinib and HER2/HER3 targeting antibody. In some aspects, step (a) comprises (i) obtaining or having obtained a biological sample from the patient; and (ii) performing or having performed an assay on the biological sample to determine the patient's cancer has an NRG1 fusion In one embodiment, provided herein are methods of treating a patient having a cancer, the method comprising administering to the patient a combined therapeutically effective amount of poziotinib and a HER2/HER3 targeting antibody, wherein the cancer has an NRG1 fusion. In one embodiment, provided herein are compositions comprising a therapeutically effective amount of poziotinib and a HER2/HER3 targeting antibody, for use in the treatment of cancer in a patient, wherein the patient's cancer has an NRG1 fusion.

In one embodiment, provided herein are methods of selecting a patient having a cancer for treatment with poziotinib and HER2/HER3 targeting antibody, the method comprising (a) determining or having determined whether the patient's cancer has an NRG1 fusion; (b) selecting or having selected the patient for treatment with poziotinib and a HER2/HER3 targeting antibody when the patient's cancer has an NRG1 fusion. In some aspects, step (a) comprises (i) obtaining or having obtained a biological sample from the patient; and (ii) performing or having performed an assay on the biological sample to determine the patient's cancer has an NRG1 fusion. In some aspects, the methods further comprise (c) administering or having administered to the selected patient a combined therapeutically effective amount of poziotinib and a HER2/HER3 targeting antibody.

In some aspects of any of the embodiments, the NRG1 fusion is an NRG1-DOC4 fusion, an NRG1-VAMP2 fusion, an NRG1-CLU fusion, an NRG1-SLC3A2 fusion, an NRG1-CD74 fusion, an NRG1-ATP1B1 fusion, or an NRG1-SDC4 fusion.

In some aspects of any of the embodiments, the methods further comprise administering to the patient an HER2/HER3 targeting antibody. In some aspects, the HER2/HER3 targeting antibody comprises trastuzumab, pertuzumab, or T-DM1.

In some aspects of any of the embodiments, the methods further comprise administering a further anti-cancer therapy to the patient. In some aspects, the further anti-cancer therapy is a surgical therapy, a chemotherapy, a radiation therapy, a cryotherapy, a hormonal therapy, a toxin therapy, an immunotherapy, or a cytokine therapy.

In some aspects of any of the embodiments, the cancer is a breast cancer, a lung cancer, a colorectal cancer, a neuroblastoma, a pancreatic cancer, a brain cancer, a stomach cancer, a skin cancer, a testicular cancer, a prostate cancer, an ovarian cancer, a liver cancer, an esophageal cancer, a cervical cancer, a head and neck cancer, a melanoma, or a glioblastoma. In some aspects, the cancer is a breast cancer or a lung cancer.

In some aspects of any of the embodiments, the patient has previously undergone at least one round of anti-cancer therapy. In some aspects of any of the embodiments, the methods further comprise reporting the presence of an NRG1 fusion in the patient's cancer. In some aspects, reporting comprises preparing a written or electronic report. In some aspects, the methods further comprise providing the report to the subject, a doctor, a hospital, or an insurance company.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
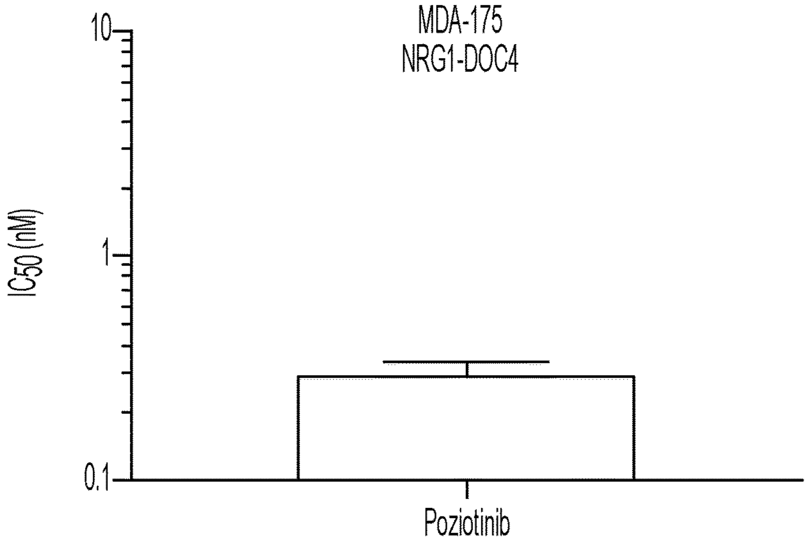
FIG. 1. Bar graph of $IC_{50}$ values of MDA175-VII (NRG1-DOC4 fusion) treated with poziotinib for 72 hours.

Provided herein are methods for treating cancer patients with NRG1 fusions. In particular, the present methods comprise the administration of poziotinib (also known as HM781-36B), either alone or in combination with a HER2/HER3 targeting antibody, to cancer patients identified as having an NRG1 fusion. In addition, the present methods comprise the identification and selection of cancer patients likely to benefit from the administration of poziotinib, either alone or in combination with a HER2/HER3 targeting antibody, by determining whether the patient's cancer has an NRG1 fusion.

I. NRG1 FUSIONS

An NRG1 fusion gene comprises at least a portion of the NRG1-gene fused to a sequence from a different chromosomal location. "At least a portion" indicates that the entire NRG1 gene may be present in a fusion or a portion thereof. The fusion may have at least the coding sequence of exons 6, 7, and 8 of NRG1. Another way to define the NRG1 portion in the NRG1-fusion gene is that it comprises the EGF-like domain of NRG1. The EGF-like domain is encoded by the 3' end of the gene and is necessary for binding to ErbB-3. The NRG1-fusions retain an in-frame coding region for the EGF-like domain. The portion of the NRG1 gene may be fused to a sequence from a different chromosomal location such that the said sequence is located 5' or 3' to the portion of the NRG1 gene.

Preferably, the 3' end of the NRG1-gene may be fused to a sequence from a different chromosomal location. In particular, the NRG1 fusion gene may be a fusion of the 3' end of the NRG1-gene with the 5' sequence of one of the genes selected from the group consisting of DOC4 (also known as Teneurin Transmembrane Protein 4 (TENM4); Protein Odd Oz/Ten-M Homolog 4; Tenascin-M4; Ten-M4; Ten-4; ODZ4; TNM4; Odz, Odd Oz/Ten-M Homolog 4 (*Drosophila*); Odz, Odd OzAen-M Homolog 4; Teneurin-4; KIAA1302; Doc4; ETMS; HGNC: 29945; Entrez Gene: 26011; Ensembl: ENSG00000149256; OMIM: 610084; and UniProtKB: Q6N022); CD74 (also known as CD74 Molecule; CD74 Antigen (Invariant Polypeptide Of Major Histocompatibility Complex, Class II Antigen-Associated); CD74 Molecule, Major Histocompatibility Complex, Class II Invariant Chain; HLA-DR Antigens-Associated Invariant Chain; Gamma Chain Of Class II Antigens; la-Associated Invariant Chain; MEW HLA-DR Gamma Chain; HLA-DR-Gamma; DHLAG; P33; HLA Class II Histocompatibility Antigen Gamma Chain; la Antigen-Associated Invariant Chain; la-GAMMA; HLADG; HGNC: 1697; Entrez Gene: 972; Ensembl: ENSG00000019582; OMIM: 142790, and UniProtKB: P04233); TNFRSF10B (also known as TNF Receptor Superfamily Member 10b; Tumor Necrosis Factor Receptor Superfamily, Member 10b; TNF-Related Apoptosis-Inducing Ligand Receptor 2; Death Receptor 5; TRAIL-R2; TRAILR2; KILLER; TRICK2; ZTNFR9; DR5; P53-

Regulated DNA Damage inducible Cell Death Receptor (Killer); Tumor Necrosis Factor Receptor Superfamily Member 10B; Tumor Necrosis Factor Receptor-Like Protein ZTNFR9; Death Domain Containing Receptor For TRAIL/Apo-2L; Apoptosis Inducing Protein TRICK2A/2B; Apoptosis Inducing Receptor TRAIL-R2; Cytotoxic TRAIL Receptor-2; Fas-Like Protein; TRAIL Receptor 2; CD262 Antigen; KILLER/DR5; TRICK2A; TRICK2B; TRICKB; CD262; HGNC: 11905; Entrez Gene: 8795; Ensembl: ENSG00000120889; OMIM: 603612; and UniProtKB: 014763); CLU (also known as Clusterin; Testosterone-Repressed Prostate Message 2; Apolipoprotein J; Complement-Associated Protein SP-40,40; Complement Cytolysis Inhibitor; Complement Lysis Inhibitor; Sulfated Glycoprotein 2; Ku70-Binding Protein 1; NA1/NA2; TRPM-2; APO-J; APOJ; KUB1; CLI; Clusterin (Complement Lysis Inhibitor, SP-40,40, Sulfated Glycoprotein 2, Testosterone-Repressed Prostate Message 2, Apolipoprotein J); Aging-Associated Gene 4 Protein; Aging-Associated Protein 4; SGP-2; SP-40; TRPM2; AAG4; CLU1; CLU2; SGP2; HGNC: 2095; Entrez Gene: 1191; Ensembl: ENSG00000120885; OMIM: 185430; and UniProtKB: P10909); VAMP2 (also known as Vesicle Associated Membrane Protein 2; synaptobrevin 2; SYB2; Vesicle-Associated Membrane Protein 2; Synaptobrevin-2; HGNC: 12643; Entrez Gene: 6844; Ensembl: ENSG00000220205; OMIM: 185881; and UniProtKB: P63027); SLC3A2 (also known as Solute Carrier Family 3 Member 2; Lymphocyte Activation Antigen 4F2 Large Subunit; Solute Carrier Family 3 (Activators Of Dibasic And Neutral Amino Acid Transport), Member 2; Antigen Identified By Monoclonal Antibodies 4F2, TRA1.10, TROP4, And T43; Solute Carrier Family 3 (Amino Acid Transporter Heavy Chain), Member 2; 4F2 Cell-Surface Antigen Heavy Chain; CD98 Heavy Chain; 4F2HC; MDU1; Antigen Defined By Monoclonal Antibody 4F2, Heavy Chain; Antigen Defined By Monoclonal Antibody 4F2; 4F2 Heavy Cham Antigen; 4F2 Heavy Chain; CD98 Antigen; CD98HC; 4T2HC; NACAE; CD98; 4F2; HGNC: 11026; Entrez Gene: 6520; Ensembl: ENSG00000168003; OMIM: 158070; and UniProtKB: P08195); RBPMS (also known as RNA Binding Protein With Multiple Splicing; Heart And RRM Expressed Sequence; HERMES; RNA-Binding Protein With Multiple Splicing; RBP-MS; HGNC: 19097; Entrez Gene: 11030; Ensembl: ENSG00000157110; OMIM: 601558; and UniProtKB: Q93062); WRN (also known as Werner Syndrome RecQ Like Helicase; DNA Helicase, RecQ-Like Type 3; RecQ Protein-Like 2; Exonuclease WRN; RECQL2; RECQ3; Werner Syndrome ATP-Dependent Helicase; Werner Syndrome, RecQ Helicase-Like; Werner Syndrome; EC 3.6.4.12; EC 3.1.-.-; EC 3.6.1; RECQL3; HGNC: 12791; Entrez Gene: 7486; Ensembl: ENSG00000165392; OMIM: 604611 and UniProtKB: Q14191); SDC4 (also known as Syndecan 4 (Amphiglycan, Ryudocan); Syndecan Proteoglycan 4; Ryudocan Core Protein; Amphiglycan; SYND4; Ryudocan Amphiglycan; Syndecan-4; HGNC: 10661; Entrez Gene: 6385; Ensembl: ENSG00000124145; OMIM: 600017; and UniProtKB: P31431); KIF13B; SLECA2; PDE7A; ATP1B1; CDK1; BMPRIB; MCPH1; and RAB2IL1.

Certain embodiments of the present disclosure concern determining if a subject has an NRG1 fusion. Detection methods are known the art including PCR analyses, nucleic acid sequencing, fluorescence in situ hybridization (FISH), chromogenic in situ hybridization (CISH), and comparative genomic hybridization (CGH).

Samples that are suitable for use in the methods described herein contain genetic material, e.g., genomic DNA (gDNA). Genomic DNA is typically extracted from biological samples such as blood or mucosal scrapings of the lining of the mouth, but can be extracted from other biological samples including urine, tumor, or expectorant. The sample itself will typically include nucleated cells (e.g., blood or buccal cells) or tissue removed from the subject, including tumor tissue. Methods and reagents are known in the art for obtaining, processing, and analyzing samples. In some embodiments, the sample is obtained with the assistance of a health care provider, e.g., to draw blood or take a tumor biopsy. In some embodiments, the sample is obtained without the assistance of a health care provider, e.g., where the sample is obtained non-invasively, such as a sample comprising buccal cells that is obtained using a buccal swab or brush, or a mouthwash sample.

In particular, the patient sample can be any bodily tissue or fluid that includes nucleic acids from the cancer in the subject. In certain embodiments, the sample will be a blood sample comprising circulating tumor cells or cell-free DNA. In other embodiments, the sample can be a tissue, such as a tumor tissue. The tumor tissue may be fresh frozen or formalin-fixed, paraffin-embedded (FFPE).

In some cases, a biological sample may be processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) or the Wizard® Genomic DNA purification kit (Promega).

Amplification of nucleic acids, where desirable, can be accomplished using methods known in the art, e.g., PCR. In one example, a sample (e.g., a sample comprising genomic DNA), is obtained from a subject. The DNA in the sample is then examined to determine the identity of an NRG1 fusion as described herein. An NRG1 fusion can be detected by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular NRG1 fusion.

A set of probes typically refers to a set of primers, usually primer pairs, and/or detectably-labeled probes that are used to detect the target genetic variations (e.g., NRG1 fusions) used in the actionable treatment recommendations of the present disclosure. The primer pairs are used in an amplification reaction to define an amplicon that corresponds to an NRG1 fusion. The set of amplicons are detected by a set of matched probes. In an exemplary embodiment, the present methods may use TaqMan™ (Roche Molecular Systems, Pleasanton, Calif.) assays that are used to detect a set of target genetic variations, such as NRG1 fusions. In one embodiment, the set of probes are a set of primers used to generate amplicons that are detected by a nucleic acid sequencing reaction, such as a next generation sequencing reaction. In these embodiments, for example, AmpliSEQ™ (Life Technologies/Ion Torrent, Carlsbad, Calif.) or TruSEQ™ (Illumina, San Diego, Calif.) technology can be employed.

Analysis of nucleic acid markers can be performed using techniques known in the art including, without limitation, sequence analysis, and electrophoretic analysis. Non-limiting examples of sequence analysis include Maxam-Gilbert sequencing, Sanger sequencing, capillary array DNA sequencing, thermal cycle sequencing, solid-phase sequencing, sequencing with mass spectrometry such as matrix-assisted laser desorption/ionization time-of-flight mass spectrometry (MALDI-TOF/MS), and sequencing by hybridization. Non-limiting examples of electrophoretic analysis include slab gel electrophoresis such as agarose or polyacrylamide gel electrophoresis, capillary electrophoresis, and denaturing gradient gel electrophoresis. Additionally, next generation sequencing methods can be performed using commercially available kits and instruments from companies such as the Life Technologies/Ion Torrent PGM or Proton, the Illumina HiSEQ or MiSEQ, and the Roche/454 next generation sequencing system.

Other methods of nucleic acid analysis can include direct manual sequencing (U.S. Pat. No. 5,288,644); automated fluorescent sequencing; single-stranded conformation polymorphism assays (SSCP); clamped denaturing gel electrophoresis (CDGE); two-dimensional gel electrophoresis (2DGE or TDGE); conformational sensitive gel electrophoresis (CSGE); denaturing gradient gel electrophoresis (DGGE); denaturing high performance liquid chromatography (DHPLC); infrared matrix-assisted laser desorption/ionization (IR-MALDI) mass spectrometry; mobility shift analysis; restriction enzyme analysis; quantitative real-time PCR; heteroduplex analysis; chemical mismatch cleavage (CMC); RNase protection assays; use of polypeptides that recognize nucleotide mismatches, e.g., *E. coli* mutS protein; allele-specific PCR, and combinations of such methods. See, e.g., U.S. Patent Publication No. 2004/0014095, which is incorporated herein by reference in its entirety.

In one example, a method of identifying an NRG1 fusion in a sample comprises contacting a nucleic acid from said sample with a nucleic acid probe that is capable of specifically hybridizing to a nucleic acid encoding an NRG1 fusion and detecting said hybridization. In a particular embodiment, said probe is detectably labeled such as with a radioisotope ($^{3}H$, $^{32}P$, or $^{33}P$), a fluorescent agent (rhodamine, or fluorescein) or a chromogenic agent. In a particular embodiment, the probe is an antisense oligomer, for example PNA, morpholino-phosphoramidates, LNA or 2'-alkoxyalkoxy. The probe may be from about 8 nucleotides to about 100 nucleotides, or about 10 to about 75, or about 15 to about 50, or about 20 to about 30. In another aspect, said probes of the present disclosure are provided in a kit for identifying NRG1 fusions in a sample, said kit comprising oligonucleotides that specifically hybridize to specific NRG1 fusions. The kit may further comprise instructions for treating patients having tumors that contain NRG1 fusion with poziotinib, either alone or in combination with HER2/HER3 targeting antibodies, based on the result of a hybridization test using the kit.

II. HER2/HER3 TARGETING ANTIBODIES

A "HER2/HER3 targeting antibody" as used herein includes any molecule that interferes with the function of HER2 and/or HER3. Thus, HER2/HER3 targeting antibody includes an anti-HER2 antibody (e.g., trastuzumab or pertuzumab), an anti-HER3 antibody, and an anti-HER2/HER3 bispecific antibody (e.g., the antibodies disclosed in WO2018/182422 or MCLA-128). A HER2/HER3 targeting antibody may prevent the formation of HER2/HER2 dimers and/or HER2/HER3 dimers (e.g., trastuzumab or pertuzumab). In some cases, a HER2/HER3 targeting antibody may be an antibody drug conjugate (e.g., T-DM1 or U3-1402).

In certain embodiments, the HER2/HER3 targeting antibody is trastuzumab (Genentech and Roche), trastuzumab emtansine (T-DM1; Genentech and Roche), pertuzumab (Genentech), ertumaxomab (Fresenius), margetuximab (MacroGenics), MCLA-128 (zenocutuzumab; Merus) MM-111 (Merrimack), MM-121 (Merrimack), CT-P06 (Celltrion), GSK2849330 (GlaxoSmithKline), PF-05280014 (Pfizer), MM-302 (Merrimack), SB3 (Merck & Co), CMAB302 (Shanghai CP Guojian), RG7116 (lemretuzumab; Genentech/Roche), TrasGEX (Glycotope), ARX788 (Ambrx and Zhejiang Medicine), SYD985 (Synthon), FS102 (Bristol-Myers Squibb and f-star), BCD-022 (Biocad), ABP 980 (Amgen), DS-8201a (Daiichi Sankyo), HLX02 (Shanghai Henlius), SAR256212 (Sanofi Oncology), RG7597 (Genentech), U3-1402 (Daiichi Sankyo), or CANMAb (Biocon and Mylan).

Trastuzumab (CAS 180288-69-1, HERCEPTIN®, huMAb4D5-8, rhuMAb HER2, Genentech) is a humanized, IgG1 kappa, monoclonal antibody that selectively binds with high affinity to the extracellular domain of the human epidermal growth factor receptor 2 protein, HER2 (ErbB2) (U.S. Pat. Nos. 5,677,171; 5,821,337; 6,054,297; 6,165,464; 6,339,142; 6,407,213; 6,639,055; 6,719,971; 6,800,738; 7,074,404). Trastuzumab contains human framework regions with the complementarity-determining regions of a murine antibody (4D5) that binds to HER2. Trastuzumab binds to the HER2 antigen and thus inhibits the growth of cancerous cells. Trastuzumab has been shown, in both in vitro assays and in animals, to inhibit the proliferation of human tumor cells that overexpress HER2. Trastuzumab is a mediator of antibody-dependent cellular cytotoxicity, ADCC.

Trastuzumab emtansine, also known as ado-trastuzumab emtansine and sold under the trade name KADCYLA®, is an antibody-drug conjugate consisting of the humanized monoclonal antibody trastuzumab covalently linked to the cytotoxic agent emtansine (DM1). Trastuzumab alone stops growth of cancer cells by binding to the HER2 receptor, whereas trastuzumab emtansine undergoes receptor-mediated internalization into cells, is catabolized in lysosomes where DM1-containing catabolites are released and subsequently bind tubulin to cause mitotic arrest and cell death. Trastuzumab binding to HER2 prevents homodimerization or heterodimerization (HER2/HER3) of the receptor, ultimately inhibiting the activation of MAPK and PI3K/AKT cellular signaling pathways. Because the monoclonal antibody targets HER2, and HER2 is only over-expressed in cancer cells, the conjugate delivers the cytotoxic agent DM1 specifically to tumor cells. The conjugate is abbreviated T-DM1. T-DM1 may be administered at a dose of 2-3 mg/kg, such as 3.6 mg/kg. The T-DM1 may be administered by intravenous infusion.

Pertuzumab (CAS Reg. No. 380610-27-5, OMNITARG®, 2C4, Genentech) is a recombinant, humanized monoclonal antibody that inhibits dimerization of HER2 (U.S. Pat. Nos. 6,054,297; 6,407,213; 6,800,738; 6,627,196, 6,949,245; 7,041,292). Pertuzumab contains the human IgG1 (x) framework sequences. Pertuzumab and trastuzumab target different extracellular regions of the HER2 tyrosine kinase receptor. Pertuzumab binds to an epitope within sub-domain 2 of HER2, while the epitope from trastuzumab is localized to sub-domain 4. Pertuzumab blocks the ability of the HER2 receptor to collaborate with other HER receptor family members, i.e., HER1/EGFR, HER3, and HER4 (U.S. Pat. No. 6,949,245). In cancer cells, interfering with the ability of HER2 to collaborate with other HER family receptors blocks cell signaling and may ultimately lead to cancer cell growth inhibition and death of the cancer cell.

Additional exemplary HER2/HER3 targeting antibodies include MM-121/SAR256212, which is a fully human monoclonal antibody that targets the HER3 receptor and which has been reported to be useful in the treatment of non-small cell lung cancer (NSCLC), breast cancer and ovarian cancer. SAR256212 is an investigational fully human monoclonal antibody that targets the HER3 (ErbB3) receptor. Duligotuzmab (MEHD7945A, RG7597) is a humanized IgG1 monoclonal antibody that targets HER1 and HER3, and has been described as being useful in head and neck cancers. Margetuximab (MGAH22) is an Fc-optimized monoclonal antibody that targets HER2.

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. Various techniques known to persons of ordinary skill in the art can be used to determine whether an antibody interacts with a polypeptide or protein. Exemplary techniques include, for example, routine cross-blocking assays. Cross-blocking can be measured in various binding assays such as ELISA, biolayer interferometry, or surface plasmon resonance. Other methods include alanine scanning mutational analysis, peptide blot analysis, peptide cleavage analysis, high-resolution electron microscopy techniques using single particle reconstruction, cryoEM, or tomography, crystallographic studies, and NMR analysis.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay. Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, the antibodies may be defined by their variable sequence, which include additional "framework" regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below).

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Wash. D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-

425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art.

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

III. METHODS OF TREATMENT

The present invention provides methods of treating a cancer patient with poziotinib, either alone or in combination with a HER2/HER3 targeting antibody. Such treatment may also be in combination with another therapeutic regime, such as chemotherapy or immunotherapy. Certain aspects of the present invention can be used to select a cancer patient for treatment based on the presence of an NRG1 fusion in the patient's cancer cells. In various aspects, about 5%, 10%, 15%, 20%, 25%, 30%, 35%, 40%, 45%, 50%, 55%, 60%, 65%, 70%, 75%, 80%, 85%, 90%, 95%, or 100% of the cells that comprise the cancer may harbor an NRG1 fusion, which indicates that the patient is a candidate for treatment. In some aspects, the patient's cancer cells lack a mutation at EGFR T790 and/or at EGFR C797. In some aspects, the patient's cancer cells lack a mutation at HER2 T798 and/or at HER2 C805.

In certain aspects, the subject was determined to have an NRG1 fusion by analyzing a genomic sample from the subject. In some aspects, the genomic sample is isolated from saliva, blood, urine, or tumor tissue. In particular aspects, the presence of an NRG1 fusion is determined by nucleic acid sequencing (e.g., DNA sequencing of tumor tissue or circulating free DNA from plasma) or PCR analyses.

Certain embodiments concern the administration of poziotinib (also known as HM781-36B, HM781-36, and 1-[4-[4-(3,4-dichloro-2-fluoroanilino)-7-methoxyquinazolin-6-yl]oxypiperidin-1-yl]prop-2-en-1-one) to a subject determined to have an NRG1 fusion. Poziotinib is a quinazoline-based pan-HER inhibitor that irreversibly blocks signaling through the HER family of tyrosine-kinase receptors including HER1, HER2, and HER4. Poziotinib or structurally similar compounds (e.g., U.S. Pat. No. 8,188,102 and U.S. Patent Publication No. 20130071452; incorporated herein by reference) may be used in the present methods.

In some aspects, the poziotinib is further defined as poziotinib hydrochloride salt. In certain aspects, the poziotinib hydrochloride salt is formulated as a tablet. The poziotinib may be administered orally, such as in a tablet. The poziotinib may be administered in a dose of 4-25 mg, such as at a dose of 5, 6, 7, 8, 9, 10, 11, 12, 13, 14, 15, 16, 17, 18, 19, 20, 21, 22, 23, 24, or 25 mg. In certain aspects, the poziotinib is administered at a dose of 6 mg, 8 mg, 12 mg, or 16 mg. The dosing may be twice per day, daily, every other day, every 3 days or weekly. The dosing may be on a continuous schedule, such as on 28 days cycles.

In certain aspects, the poziotinib and/or HER2/HER3 targeting antibody are administered intravenously, subcutaneously, intraosseously, orally, transdermally, in sustained release, in controlled release, in delayed release, as a suppository, or sublingually. In some aspects, administering the poziotinib and/or HER2/HER3 targeting antibody comprises local, regional or systemic administration. In particular aspects, the poziotinib and/or HER2/HER3 targeting antibody are administered two or more times, such as daily, every other day, or weekly.

In some aspects, the poziotinib is administered prior to or after the HER2/HER3 targeting antibody, such as 1 day, 2 days, 3 days, 4 days, 5 days, 6 days, 7 days, 2 weeks, 3 weeks, 1 month or more apart. In some aspects, the poziotinib is administered simultaneously with the HER2/HER3 targeting antibody.

The term "subject" or "patient" as used herein refers to any individual to which the subject methods are performed. Generally the patient is human, although as will be appreciated by those in the art, the patient may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The methods described herein are useful in inhibiting survival or proliferation of cells (e.g., tumor cells), treating proliferative disease (e.g., cancer, psoriasis), and treating pathogenic infection. Generally, the terms "cancer" and "cancerous" refer to or describe the physiological condition in mammals that is typically characterized by unregulated cell growth. More specifically, cancers that are treated in connection with the methods provided herein include, but are not limited to, solid tumors, metastatic cancers, or non-metastatic cancers. In certain embodiments, the cancer may originate in the lung, kidney, bladder, blood, bone, bone marrow, brain, breast, colon, esophagus, duodenum, small intestine, large intestine, colon, rectum, anus, gum, head, liver, nasopharynx, neck, ovary, pancreas, prostate, skin, stomach, testis, tongue, or uterus.

The cancer may specifically be of the following histological type, though it is not limited to these: neoplasm, malignant; carcinoma; non-small cell lung cancer; renal cancer; renal cell carcinoma; clear cell renal cell carcinoma; lymphoma; blastoma; sarcoma; carcinoma, undifferentiated; meningioma; brain cancer; oropharyngeal cancer; nasopharyngeal cancer; biliary cancer; pheochromocytoma; pancreatic islet cell cancer; Li-Fraumeni tumor; thyroid cancer; parathyroid cancer; pituitary tumor; adrenal gland tumor; osteogenic sarcoma tumor; neuroendocrine tumor; breast cancer; lung cancer; head and neck cancer; prostate cancer; esophageal cancer; tracheal cancer; liver cancer; bladder cancer; stomach cancer; pancreatic cancer; ovarian cancer; uterine cancer; cervical cancer; testicular cancer; colon cancer; rectal cancer; skin cancer; giant and spindle cell carcinoma; small cell carcinoma; small cell lung cancer; papillary carcinoma; oral cancer; oropharyngeal cancer; nasopharyngeal cancer; respiratory cancer; urogenital cancer; squamous cell carcinoma; lymphoepithelial carcinoma; basal cell carcinoma; pilomatrix carcinoma; transitional cell carcinoma; papillary transitional cell carcinoma; adenocarcinoma; gastrointestinal cancer; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma with squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; lentigo maligna melanoma; acral lentiginous melanoma; nodular melanoma; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; an endocrine or neuroendocrine cancer or hematopoietic cancer; pinealoma, malignant; chordoma; central or peripheral nervous system tissue cancer; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; B-cell lymphoma; malignant lymphoma; Hodgkin's disease; Hodgkin's; low grade/follicular non-Hodgkin's lymphoma; paragranuloma; malignant lymphoma, small lymphocytic; malignant lymphoma, large cell, diffuse; malignant lymphoma, follicular; mycosis fungoides; mantle cell lymphoma; Waldenstrom's macroglobulinemia; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; chronic lymphocytic leukemia (CLL); acute lymphoblastic leukemia (ALL); Hairy cell leukemia; chronic myeloblastic leukemia; and hairy cell leukemia.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

Likewise, an effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, previous therapy, the patient's clinical history and response to the agent, and the discretion of the physician. The agent may be suitably administered to the patient at one time or over a series of treatments.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

An anti-cancer first treatment may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations, it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below, either (a) poziotinib is “A” and a HER2/HER3 targeting antibody is “B” or (b) poziotinib, either alone or in combination with a HER2/HER3 targeting antibody, is “A” and another anti-cancer therapy is “B”:

A/B/A B/A/B B/B/A A/A/B A/B/B B/A/A A/BBB B/A/B/B

BBB/A BB/AB A/A/B/B AB/AB A/B/B/A B/B/A/A

B/A/B/A B/A/A/B A/A/A/B B/A/A/A A/B/A/A A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present invention. The term “chemotherapy” refers to the use of drugs to treat cancer. A “chemotherapeutic agent” is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antibiotic chromophores, ad acinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside (“Ara-C”); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DFMO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, Infection Immun., 66(11):5329-5336, 1998; Christodoulides et al., Microbiology, 144(Pt 11):3027-3037, 1998); cytokine therapy, e.g., interferons $\alpha$, $\beta$, and $\gamma$, IL-1, GM-CSF, and TNF (Bukowski et al., Clinical Cancer Res., 4(10):2337-2347, 1998; Davidson et al., J. Immunother., 21(5):389-398, 1998; Hellstrand et al., Acta Oncologica, 37(4):347-353, 1998); gene therapy, e.g., TNF, IL-1, IL-2, and p53 (Qin et al., Proc. Natl. Acad. Sci. USA, 95(24):14411-14416, 1998; Austin-Ward and Villaseca, Revista Medica de Chile, 126(7):838-845, 1998; U.S. Pat. Nos. 5,830,880 and 5,846,945); and monoclonal antibodies, e.g., anti-CD20, anti-ganglioside GM2, and anti-p185 (Hanibuchi et al., Int. J. Cancer, 78(4):480-485, 1998; U.S. Pat. No. 5,824,311). It is contemplated that one or more anti-cancer therapies may be employed with the antibody therapies described herein.

In some embodiment, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering. Isolation and transfer of tumor specific T cells has been shown to be successful in treating melanoma. Novel specificities in T cells have been successfully generated through the genetic transfer of transgenic T cell receptors or chimeric antigen receptors (CARs). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors.

In one embodiment, the present application provides for a combination therapy for the treatment of cancer wherein the combination therapy comprises adoptive T cell therapy and a checkpoint inhibitor. In one aspect, the adoptive T cell therapy comprises autologous and/or allogenic T-cells. In another aspect, the autologous and/or allogenic T-cells are targeted against tumor antigens.

Immunomodulatory agents include immune checkpoint inhibitors, agonists of co-stimulatory molecules, and antagonists of immune inhibitory molecules. The immunomodulatory agents may be drugs, such as small molecules, recombinant forms of ligand or receptors, or antibodies, such as human antibodies (e.g., International Patent Publication WO2015/016718; Pardoll, *Nat Rev Cancer,* 12(4): 252-264, 2012; both incorporated herein by reference). Known inhibitors of immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

Co-stimulatory molecules are ligands that interact with receptors on the surface of the immune cells, e.g., CD28, 4-1BB, OX40 (also known as CD134), ICOS, and GITR. As an example, the complete protein sequence of human OX40 has Genbank accession number NP_003318. In some embodiments, the immunomodulatory agent is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another co-stimulatory molecule that can be targeted in the methods provided herein is ICOS, also known as CD278. The complete protein sequence of human ICOS has Genbank accession number NP 036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human-ICOS antibodies (or VH and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Yet another co-stimulatory molecule that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immunomodulatory agent is an anti-GITR antibody (e.g., a human antibody, a humanized antibody, or a chimeric antibody), an antigen binding fragment thereof, an immunoadhesin, a fusion protein, or oligopeptide. Anti-human-GITR antibodies (or VH and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

Immune checkpoint proteins that may be targeted by immune checkpoint blockade include adenosine A2A receptor (A2AR), B7-H3 (also known as CD276), B and T lymphocyte attenuator (BTLA), CCLS, CD27, CD38, CD8A, CMKLR1, cytotoxic T-lymphocyte-associated protein 4 (CTLA-4, also known as CD152), CXCL9, CXCR5, HLA-DRB1, HLA-DQA1, HLA-E, killer-cell immunoglobulin (KIR), lymphocyte activation gene-3 (LAG-3, also known as CD223), Mer tyrosine kinase (MerTK), NKG7, programmed death 1 (PD-1), programmed death-ligand 1 (PD-L1, also known as CD274), PDCD1LG2, PSMB10, STAT1, T cell immunoreceptor with Ig and ITIM domains (TIGIT), T-cell immunoglobulin domain and mucin domain 3 (TIM-3), and V-domain Ig suppressor of T cell activation (VISTA, also known as C10orf54). In particular, immune checkpoint inhibitors targeting the PD-1 axis and/or CTLA-4 have received FDA approval broadly across diverse cancer types.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Application Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUIDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Another immune checkpoint protein that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA-4 is similar to the T-cell co-stimulatory protein, CD28, and both molecules bind to CD80 and CD86, also called B7-1 and B7-2 respectively, on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide. Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Publn. Nos. WO 01/14424, WO 98/42752, WO 00/37504 (CP675,206, also known as tremelimumab; formerly ticilimumab); U.S. Pat. No. 6,207,156; Hurwitz et al. (1998) *Proc Natl Acad Sci USA,* 95(17): 10067-10071; Camacho et al. (2004) *J Clin Oncology,* 22(145): Abstract No. 2505 (antibody CP-675206); and Mokyr et al. (1998) Cancer Res, 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2, and CDR3 domains of the VL region of ipilimumab. In another embodiment, the antibody competes for binding with and/or binds to the same epitope on CTLA-4 as the above-mentioned antibodies. In another embodiment, the antibody has an at least about 90% variable region amino acid sequence identity with the above-mentioned antibodies (e.g., at least about 90%, 95%, or 99% variable region identity with ipilimumab). Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank accession number NP-002277. LAG-3 is found on the surface of activated T cells, natural killer cells, B cells, and plasmacytoid dendritic cells. LAG-3 acts as an "off" switch when bound to MHC class II on the surface of antigen-presenting cells. Inhibition of LAG-3 both activates effector T cells and inhibitor regulatory T cells. In some embodiments, the immune checkpoint inhibitor is an anti-LAG-3 antibody (e.g., a human antibody, a humanized antibody, or a chimeric antibody), an antigen binding fragment thereof, an immunoadhesin, a fusion protein, or oligopeptide. Anti-human-LAG-3 antibodies (or VH and/or VL domains derived therefrom) suitable for use in the present methods can be generated using methods well known in the art. Alternatively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is V-domain Ig suppressor of T cell activation (VISTA), also known as C10orf54. The complete protein sequence of human VISTA has the Genbank accession number NP_071436. VISTA is found on white blood cells and inhibits T cell effector function. In some embodiments, the immune checkpoint inhibitor is an anti-VISTA3 antibody (e.g., a human antibody, a humanized antibody, or a chimeric antibody), an antigen binding fragment thereof, an immunoadhesin, a fusion protein, or oligopeptide. Anti-human-VISTA antibodies (or VH and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibodies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829,673).

Another immune checkpoint protein that can be targeted in the methods provided herein is T cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VH and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Other immune inhibitory molecules that can be targeted for immunomodulation include STAT3 and indoleamine 2,3-dioxygenase (IDO). By way of example, the complete protein sequence of human IDO has Genbank accession number NP_002155. In some embodiments, the immunomodulatory agent is a small molecule IDO inhibitor. Exemplary small molecules include BMS-986205, epacadostat (INCB24360), and navoximod (GDC-0919).

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs)

inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

IV. KITS

In various aspects of the invention, a kit is envisioned containing, diagnostic agents, therapeutic agents and/or delivery agents. In some embodiments, the present invention contemplates a kit for detecting an NRG1 fusion in a patient's tumor cells. In some embodiments, the present invention contemplates a kit for preparing and/or administering a therapy of the invention. The kit may comprise reagents capable of use in administering an active or effective agent(s) of the invention. Reagents of the kit may include one or more anti-cancer components of a combination therapy, as well as reagents to prepare, formulate, and/or administer the components of the invention or perform one or more steps of the inventive methods. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass. The kit may further include an instruction sheet that outlines the procedural steps of the methods, and will follow substantially the same procedures as described herein or are known to those of ordinary skill.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The cell viability of NRG1-DOC4 fusion breast cancer cell line, MDA175-VII, was tested with treatment of poziotinib with and without antibodies and antibody drug conjugates (ADCs) targeting HER2 and HER2/HER3 dimerization. Cell viability was determined by the Cell Titer Glo assay. Poziotinib potently inhibited MDA175-VII cells with an average $IC_{50}$ value of 0.287 nM (FIG. 1). These data indicate that poziotinib potently inhibits NRG1 fusions at concentrations lower than previously reported TKIs.

Figures 2A, 2B:
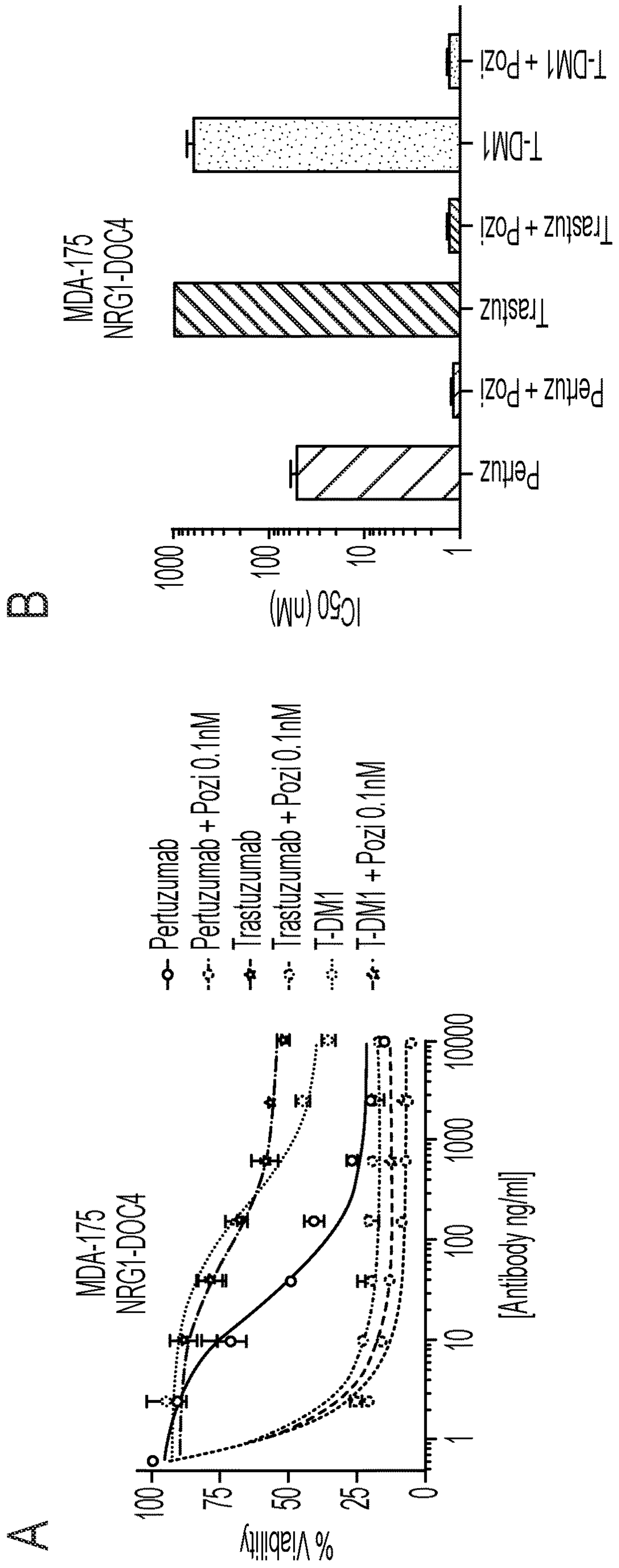
FIG. 2A. Dose response curve of MDA175-VII (NRG1-DOC4 fusion) cell line treated with the indicated HER2/HER3 antibodies with and without low dose poziotinib (0.1 nM) for 72 hours. At the 100 ng/mL value on the X-axis, the lines represent, from top to bottom, T-DM1, Trastuzumab, Pertuzumab, Trastuzumab+Poziotinib 0.1 nM, T-DM1+Poziotinib 0.1 nM, and Pertuzumab+Poziotinib 0.1 nM.
FIG. 2B. Bar graph of $IC_{50}$ values of MDA175-VII (NRG1-DOC4 fusion) cell line treated with the indicated HER2/HER3 antibodies with and without low dose poziotinib (0.1 nM) for 72 hours.

In addition, treatment with HER2 targeting antibodies trastuzumab, T-DM1, and pertuzumab had $IC_{50}$ values of >10000 ng/mL, 634.5 ng/mL, and 53.7 ng/mL, respectively (FIG. 2A). Further, the combination of HER2 antibodies with low dose poziotinib (0.1 nM) lead to increased sensitivity to trastuzumab, pertuzumab and T-DM1, reducing $IC_{50}$ values to 1.37 nM, 1.23 nM, and 1.32 nM, respectively (FIG. 2B).

Example 2

Ba/F3 cells generation. Ba/F3 cells stably co-expressing WT ErbB2 and WT ErbB3 or WT ErbB3 and WT ErbB4 are generated as previously described. Briefly, retroviral or lentiviral constructs are transfected into Phoenix 293T cells to produce virus which is incubated with Ba/F3 cell lines over night. Virus is removed and cells are cultured in puromycin for 10 days to select for Ba/F3 cell lines stably expressing retrovirus constructs. After selection, cells are sorted using anti-HER2, anti-HER3, and anti-HER4 antibodies (Biolegend). Cell lines are then transduced again with lentivirus containing NRG-fusion plasmids in Table 1A. Cells are then sorted by FACS for NRG1 expression. Stable cell lines are then deprived of IL-3. Resulting stable cell lines are used in downstream analyses including drug screening.

Drug screening and IC50 determination. Drug screening is performed as previously described. Briefly, cells are plated in 384-well plates (Greiner Bio-One) at 2000-3000 cells per well in technical triplicate. Seven different concentrations of TKIs or DMSO vehicle are added to reach a final volume of 40 μL per well. After 72 hours, 11 μL of Cell Titer Glo (Promega) is added to each well. Plates are incubated for a minimum of 10 minutes, and bioluminescence is determined using a FLUOstar OPTIMA plate reader (BMG LABTECH). Raw bioluminescence values are normalized to DMSO control treated cells, and values are plotted in GraphPad Prism. Non-linear regressions are used to fit the normalized data with a variable slope, and $IC_{50}$ values are determined by GraphPad prism by interpolation of concentrations at 50% inhibition. Drug screens are performed in technical triplicate on each plate and either duplicate or triplicate biological replicates.

Overexpression models. Overexpression models are generated by lentiviral transduction of NRG1 fusions in Table 1A. Lentiviruses are generated using Lenti-X cells Lenti-X single shot kit (Takarabio). Lenti viruses are generated as described by the manufacturer. Lentiviruses are then added to the cell lines in Table 1B. After 24 hours of viral transduction, virus is removed and cells are placed into 2 μg/ml puromycin for selection. After 10 days of selection, protein and RNA are harvested from cell lines and expression of NRG1-fusions are determined by western blotting and RT-PCR, respectively. Stable cell lines with NRG1-fusion expression are used for downstream analyses including western blotting and ELISAs.

Determination inhibition of HER signaling by western blotting and ELISA in overexpressing cell lines. Parental and overexpressing (OE) cell lines are plated in 10 cm dishes and treated with poziotinib in increasing doses from 1 nm to 100 nm. Cells are incubated with inhibitor for 4 hrs, 1 day and 3 days, and protein is harvested using lysis buffer (Cell Signaling). Expression of NRG1-fusions, phospho- and total -EGFR, HER2, HER3, and HER4 are determined by western blotting and blots are exposed using BioRad Chemidoc imager. To quantify changes in protein expression, protein from parental and OE expressing cell lines treated with poziotinib are loaded onto ELISAs (Cell Signaling), and ELISAs are completed by manufacturer instructions.

TABLE 1A

| NRG1 fusion plasmids | | |
|---|---|---|
| NRG1-CD74 | NRG1-ATP1B1 | NRG1-SLC3A2 |
| NRG1-SDC4 | NRG1-VAMP1 | NRG1-CLU |
| NRG1-RBPMS | | |

TABLE 1B

| Human cell line models | |
|---|---|
| Cell Line | Primary Tumor |
| H324 | NSCLC |
| H1819 | NSCLC |
| H2170 | NSCLC |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Drilon et al., Response to ERBB3-Directed Targeted Therapy in NRG1-Rearranged Cancers. *Cancer Discov.,* 8:686-695, 2018.

Fernandez-Cuesta et al., CD74-NRG1 fusions in lung adenocarcinoma. *Cancer Discov.,* 4:415-422, 2014.

Holbro et al., The ErbB2/ErbB3 heterodimer functions as an oncogenic unit: ErbB2 requires ErbB3 to drive breast tumor cell proliferation. *Proc. Natl. Acad. Sci. USA,* 100:8933-8938, 2003.

Jonna et al., Detection of NRG1 Gene Fusions in Solid Tumors. *Clin. Cancer Res.,* 25:4966-4972, 2019.

Jung et al., VAMP2-NRG1 Fusion Gene is a Novel Oncogenic Driver of Non-Small-Cell Lung Adenocarcinoma. *J. Thorac. Oncol.,* 10:1107-1111, 2015.

Robichaux et al., Mechanisms and clinical activity of an EGFR and HER2 exon 20-selective kinase inhibitor in non-small cell lung cancer. *Nat. Med.,* 24:638-646, 2018.

Robichaux et al., Pan-cancer landscape and functional analysis of HER2 mutations identifies poziotinib as a clinically active inhibitor and enhancer of T-DM1 activity. *Cancer Cell,* 36:444-457, 2019.

Shin et al., Dual Targeting of ERBB2/ERBB3 for the Treatment of SLC3A2-NRG1-Mediated Lung Cancer. *Mol. Cancer Ther.,* 17:2024-2033, 2018.

What is claimed is:

1. A method of treating a patient having a cancer, the method comprising administering to the patient a therapeutically effective amount of poziotinib, and a HER2/HER3 targeting antibody wherein the cancer has an NRG1 fusion.

2. The method of claim 1, wherein the NRG1 fusion is an NRG1-DOC4 fusion, an NRG1-VAMP2 fusion, an NRG1-CLU fusion, an NRG1-SLC3A2 fusion, an NRG1-CD74 fusion, an NRG1-ATP1B1 fusion, or an NRG1-SDC4 fusion.

3. The method of claim 1, wherein the HER2/HER3 targeting antibody comprises trastuzumab, pertuzumab, or T-DM1.

4. The method of claim 1, wherein the NRG1 fusion status of the cancer has been determined by performing or having performed an assay on a biological sample obtained from the patient to determine the patient's cancer has an NRG1 fusion.

5. The method of claim 1, further comprising administering a further anti-cancer therapy to the patient.

6. The method of claim 5, wherein the further anti-cancer therapy is a surgical therapy, a chemotherapy, a radiation therapy, a cryotherapy, a hormonal therapy, a toxin therapy, an immunotherapy, or a cytokine therapy.

7. The method of claim 1, wherein the cancer is a breast cancer, a lung cancer, a colorectal cancer, a neuroblastoma, a pancreatic cancer, a brain cancer, a stomach cancer, a skin cancer, a testicular cancer, a prostate cancer, an ovarian cancer, a liver cancer, an esophageal cancer, a cervical cancer, a head and neck cancer, a melanoma, or a glioblastoma.

* * * * *